United States Patent [19]
Loeffler

[11] Patent Number: 6,006,917
[45] Date of Patent: Dec. 28, 1999

[54] PACKAGING UNIT FOR ARTICLES TO BE PACKED IN STERILE CONDITION

[75] Inventor: Burkhard Loeffler, Buchenbach, Germany

[73] Assignee: Aesculap AG & Co. KG, Tuttlingen, Germany

[21] Appl. No.: 09/097,952

[22] Filed: Jun. 16, 1998

[30] Foreign Application Priority Data

Jun. 17, 1997 [DE] Germany .......................... 197 25 499

[51] Int. Cl.⁶ ................................. B65D 81/05
[52] U.S. Cl. .......................... 206/583; 206/363; 206/438
[58] Field of Search .................................. 206/363, 364, 206/438, 583, 232, 484

[56] References Cited

U.S. PATENT DOCUMENTS

| | | | |
|---|---|---|---|
| 3,853,220 | 12/1974 | Luray | 206/583 |
| 5,447,230 | 9/1995 | Gerondale | 206/438 |
| 5,678,695 | 10/1997 | Ridgeway et al. | 206/583 |

FOREIGN PATENT DOCUMENTS

| | | |
|---|---|---|
| 36 26 616 | 2/1988 | Germany . |
| 89 10 314 | 12/1989 | Germany . |
| 827346 | 1/1979 | Russian Federation ............... 206/583 |
| 657 825 | 12/1982 | Switzerland . |

*Primary Examiner*—Paul T. Sewell
*Assistant Examiner*—Luan K. Bui
*Attorney, Agent, or Firm*—Barry R. Lipsitz; Ralph F. Hoppin

[57] ABSTRACT

In a packaging unit for articles to be packed in a sterile condition, in order to reduce the risk of damage and, at the same time, to decrease the material requirement, it is proposed that it comprise an inner bag sealed in a gastight manner which surrounds the article to be packed and encloses the article in a tight manner due to evacuation, a closed outer bag which receives the inner bag, and a shape-retaining frame which holds the outer bag immovably and is insertable into a shape-retaining storage container.

32 Claims, 4 Drawing Sheets

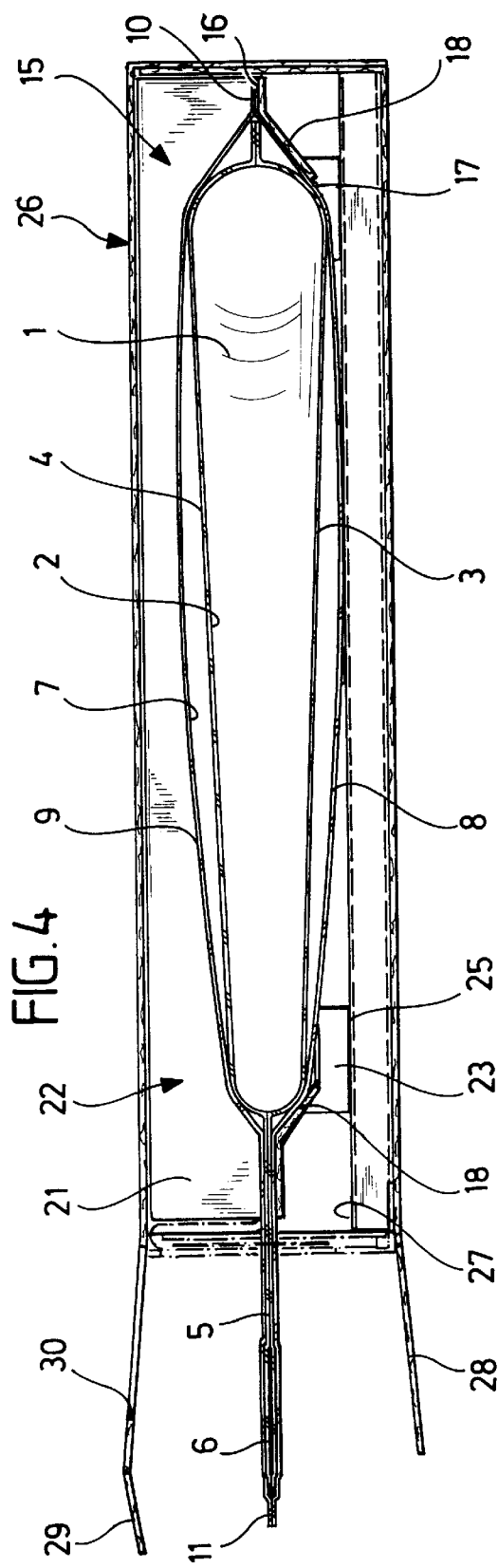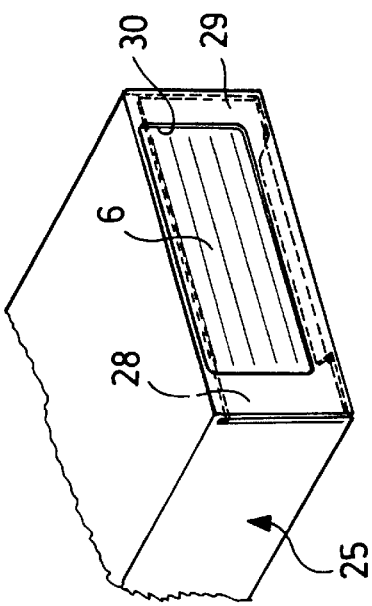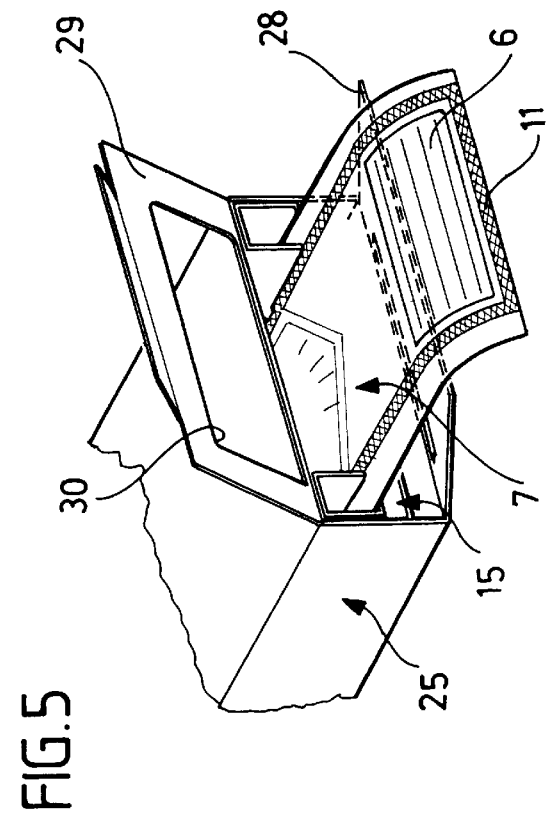

PACKAGING UNIT FOR ARTICLES TO BE PACKED IN STERILE CONDITION

The present disclosure relates to the subject matter disclosed in German application No. 197 25 499.3-27 of Jun. 17, 1997, the entire specification of which is incorporated herein by reference.

The invention relates to a packaging unit for articles to be packed in a sterile condition.

BACKGROUND OF THE INVENTION

Parts of implants and other articles used in the medical field must be packed in a sterile condition. It is known to package the articles to be packed in a sterile condition in films and to hold these films in place by means of padding or shaped inserts in storage packages. In other cases, the articles are placed in deep-drawn blisters, and the fixing in storage packages is brought about, on the one hand, by the stiffness of the deep-drawn parts and, on the other hand, by padding or shaped inserts. In all cases, the packages have to be precisely adapted to the articles to be packed. In addition, the resulting packages are bulky because of the different materials used and these are, therefore, also difficult to recycle.

SUMMARY OF THE INVENTION

The object of the invention is to create a packaging unit which is specially suited for sterile packages.

This object is accomplished in a packaging unit of the kind described at the outset in accordance with the invention in that it comprises an inner bag sealed in a gastight manner which surrounds the article to be packed and encloses the article in a tight manner due to evacuation, a closed outer bag which receives the inner bag, and a shape-retaining frame which holds the outer bag immovably and is insertable into a shape-retaining storage container.

With such a packaging unit, safe packaging of an article to be packed in a sterile condition can be achieved with a minimum of material expenditure. This packaging unit also adapts automatically to the very different shapes of the articles to be packed. Such packaging can be produced with a very small number of different materials. In principle, the inner bag and the outer bag can be made from the same film material. Similarly, the frame and the shape-retaining storage container can be of the same material, and, therefore, in principle, two different materials can suffice.

In spite of the relatively simple structure, a safe spatial fixing of the article in the storage container is achieved as the outer bag which accommodates the inner bag is immovably fixed in the frame inserted into the storage container.

It is particularly advantageous for the frame to be in the form of a slide which is slidable into the storage container.

In accordance with a preferred embodiment, provision is made for the inner bag and the outer bag to be so adapted to one another in their shape that the inner bag is immovably held in place in the outer bag. This is achievable by, for example, the outer contour of the inner bag corresponding to the inner contour of the outer bag. The article is fixed in this way in the inner bag by the evacuation, and this inner bag is fixed in the outer bag by the mutual adaptation of the bags with respect to their shape. A packaging is thus obtained which itself adapts substantially to the size and shape of the articles with very low volume and material expenditure.

In particular, provision may be made for the inner bag to consist of two film layers which are placed one on top of the other and are joined to one another along their edge, preferably so as to lie surface-to-surface against one another along an edge strip surrounding the interior.

The outer bag can be of corresponding design.

To hold the outer bag in place, it can be fixed on the frame by suitable connecting means, for example, by adhesion or with staples. In accordance with a particularly preferred embodiment, however, provision is made for the outer bag to have in the edge area thereof openings through which projections pass in order to fix the outer bag on the frame. By this clamping of the outer bag on the frame, it is held in place relative to the frame without any recesses adapted to the shape of the article to be accommodated having to be provided for this purpose.

It is expedient for the edge area containing openings to be separated from the rest of the outer bag by perforation lines. The outer bag can thereby be released from the frame without the fixing of the outer bag at the projections of the frame having to be removed. In particular, the outer bag pulled out of the frame still completely surrounds the inner bag and hence guarantees sterility of the contents of the bag.

The openings can, in particular, be arranged at opposite side strips of the outer bag.

In principle, the bags can be of any shape, but it is advantageous for the inner bag and possibly also the outer bag to be rectangular.

In a preferred embodiment, provision is made for the inner bag and/or the outer bag to carry at one side a lug-shaped extension for receiving a label. This makes it possible to designate the packed articles.

If such a lug-shaped extension is provided on the inner bag, it is expedient for it to be enclosed in a lug-shaped extension of the outer bag.

These lug-shaped extensions of the inner bag and/or the outer bag preferably protrude beyond the edge of the frame in which the two bags are held in place.

The inner bag and/or the outer bag preferably consist of a plastic film, in particular, of a material which is sterilizable by radiation.

Provision may be made for the frame to have a central opening and a holding surface which surrounds the central opening and on which the edge area of the outer bag is fixable such that the inner bag is arranged in the area of the central opening. It is thereby possible to hold the article in the frame in such a way that it itself is not supported but is merely held by the tension of the outer bag held in the frame.

The central opening can, for example, be delimited by flaps which are connected to the holding surface. In particular, these flaps are pivoted at an incline to the holding surface.

The stability of the frame can be increased by reinforcement profiles adjoining two opposite longitudinal sides of the frame. In particular, these can be formed by parallel strips which are folded over in the edge area of the holding surface and form, for example, a reinforcement profile of square cross section.

The frame can have projections formed thereon over which the openings in the outer bag are hung in order to fix it in place. In a preferred embodiment, however, provision is made for the projections for fixing the outer bag on the frame to pass through openings in the frame which are in alignment with the openings on the outer bag. Thus, in such an embodiment openings are provided in the frame which are in alignment with the openings on the outer bag, and holding means are passed through both the openings on the outer bag and the openings in the frame and then fix the outer bag on the frame.

In a preferred embodiment of the invention, these projections are formed by lugs at the free edge of the parallel, folded over strips of the reinforcement profiles.

It is expedient for the lugs to be of such length that in the state in which they pass through the openings in the outer bag and the openings in the frame they protrude downwardly beyond the holding surface of the frame and form standing legs for the frame. The lugs preferably protrude downwardly beyond the contour of the outer bag which is held in the frame and receives the inner bag with the article therein. It is thereby ensured that the bags hang completely freely in the frame without touching any adjacent edge parts.

The storage container can be block-shaped.

It is expedient for the storage container to have supporting surfaces extending parallel to its bottom for receiving the frame. It is thereby made possible to slide frames of different height into storage containers of uniform size.

Provision is made in a preferred embodiment for the storage container to be closable at its end faces by two flaps which in the closed state lie surface-to-surface against one another.

It is expedient for the outer flap to have an opening through which a flat data carrier inserted between the flaps is visible.

In particular, this data carrier may be formed by the extension of the inner bag and/or the outer bag with inserted label. Such an embodiment is particularly advantageous as only one marking is necessary, namely the marking of the label which is attached to the inner bag or the outer bag, and no additional marking is necessary for the frame or the storage container.

The frame and/or the container may preferably consist of cardboard or plastic.

The following description of preferred embodiments of the invention serves in conjunction with the appended drawings to explain the invention in greater detail.

BRIEF DESCRIPTION OF THE DRAWINGS

FIG. 4: a sectional view taken along line 4—4 in FIG. 2;

FIG. 5: a perspective partial view of an opened storage container with a frame pushed into it; and FIG. 6: a view similar to FIG. 5 of the closed storage container.

DETAILED DESCRIPTION OF THE INVENTION

Figure 1:
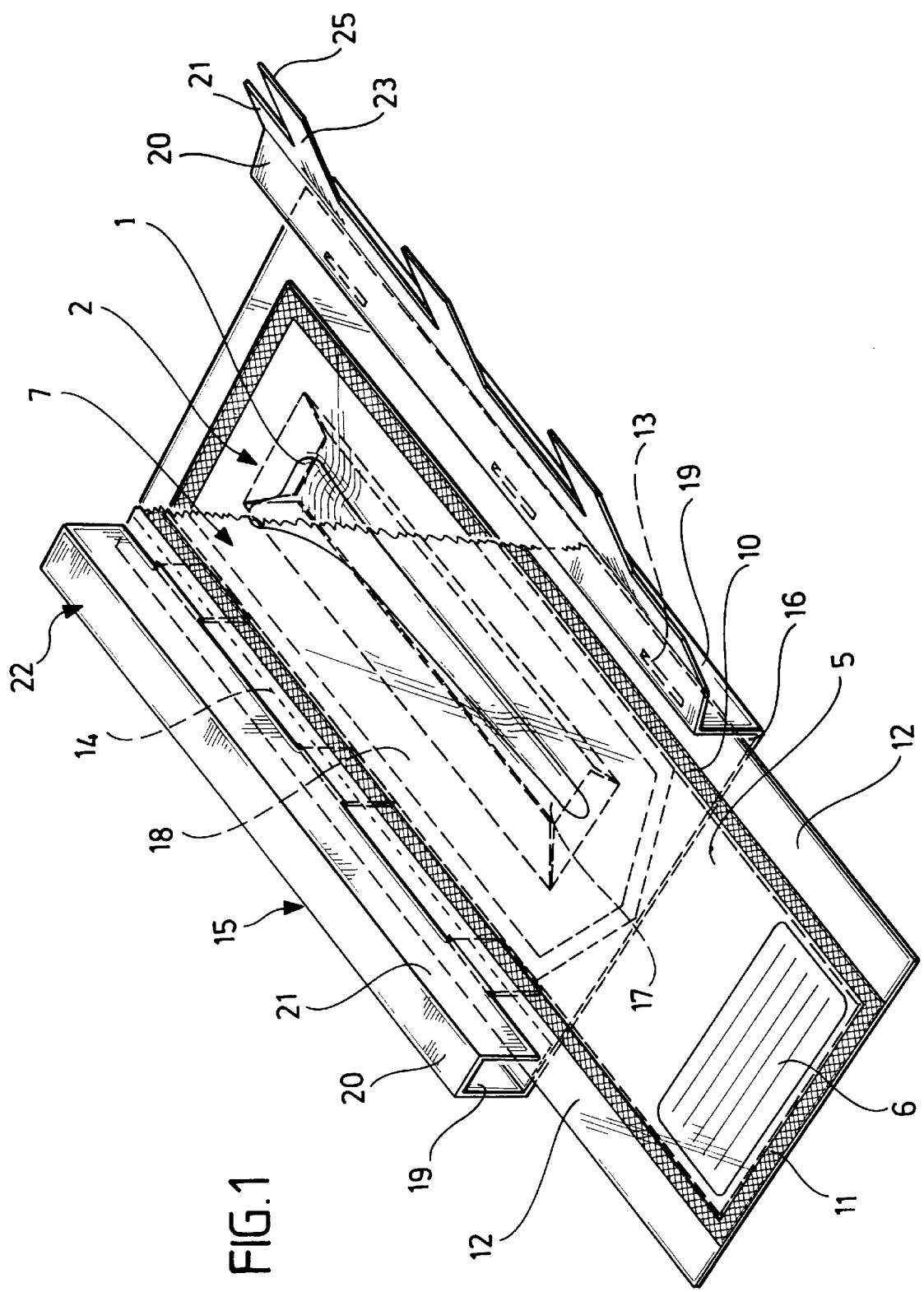
FIG. 1: a perspective plan view of a frame with an inner bag and a partly broken open outer bag which is secured to the frame at one side only.
Figure 2:
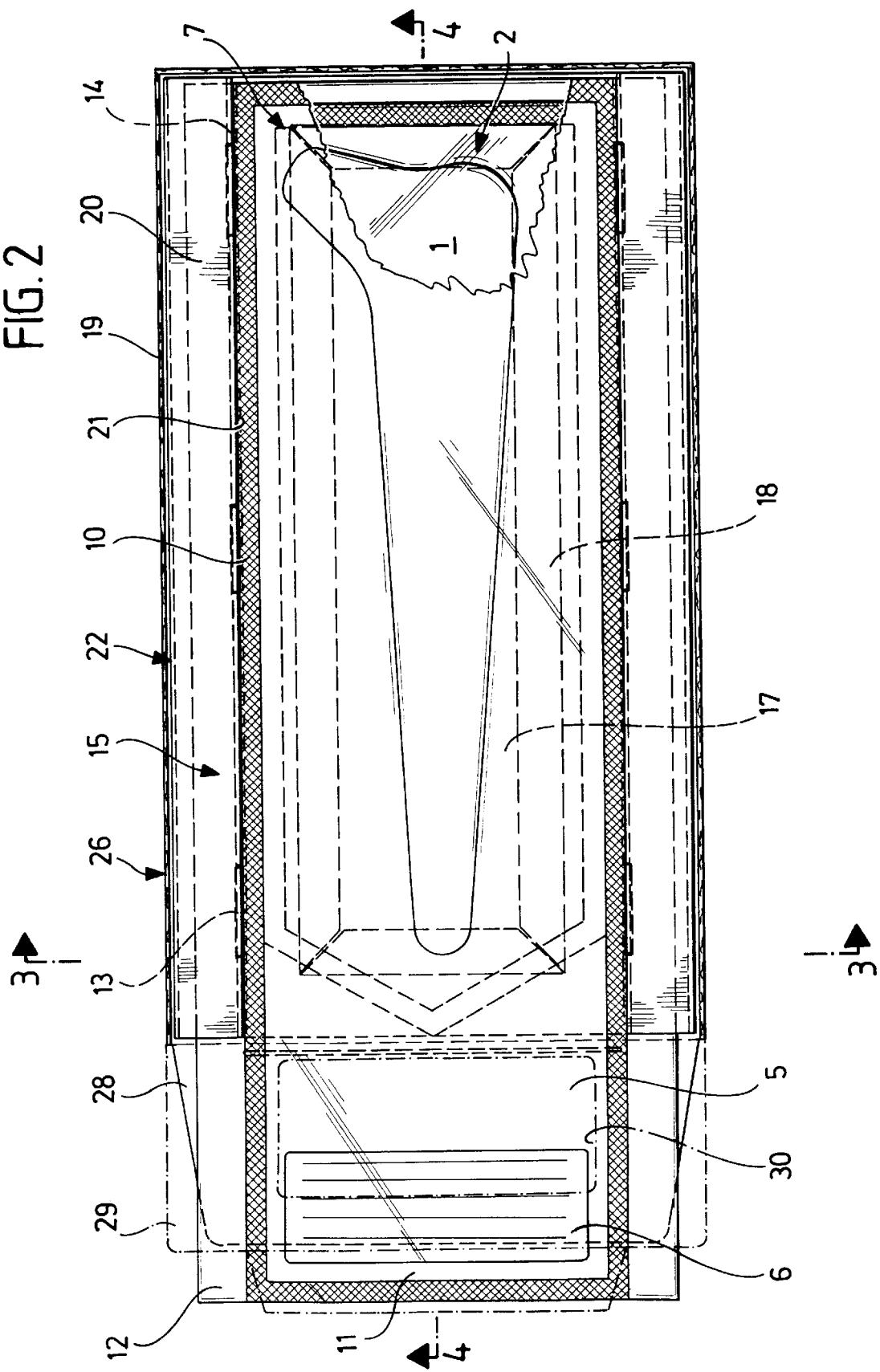
FIG. 2: a plan view of a frame with a fixed outer bag shown in broken open illustration in areas thereof.
Figure 3:
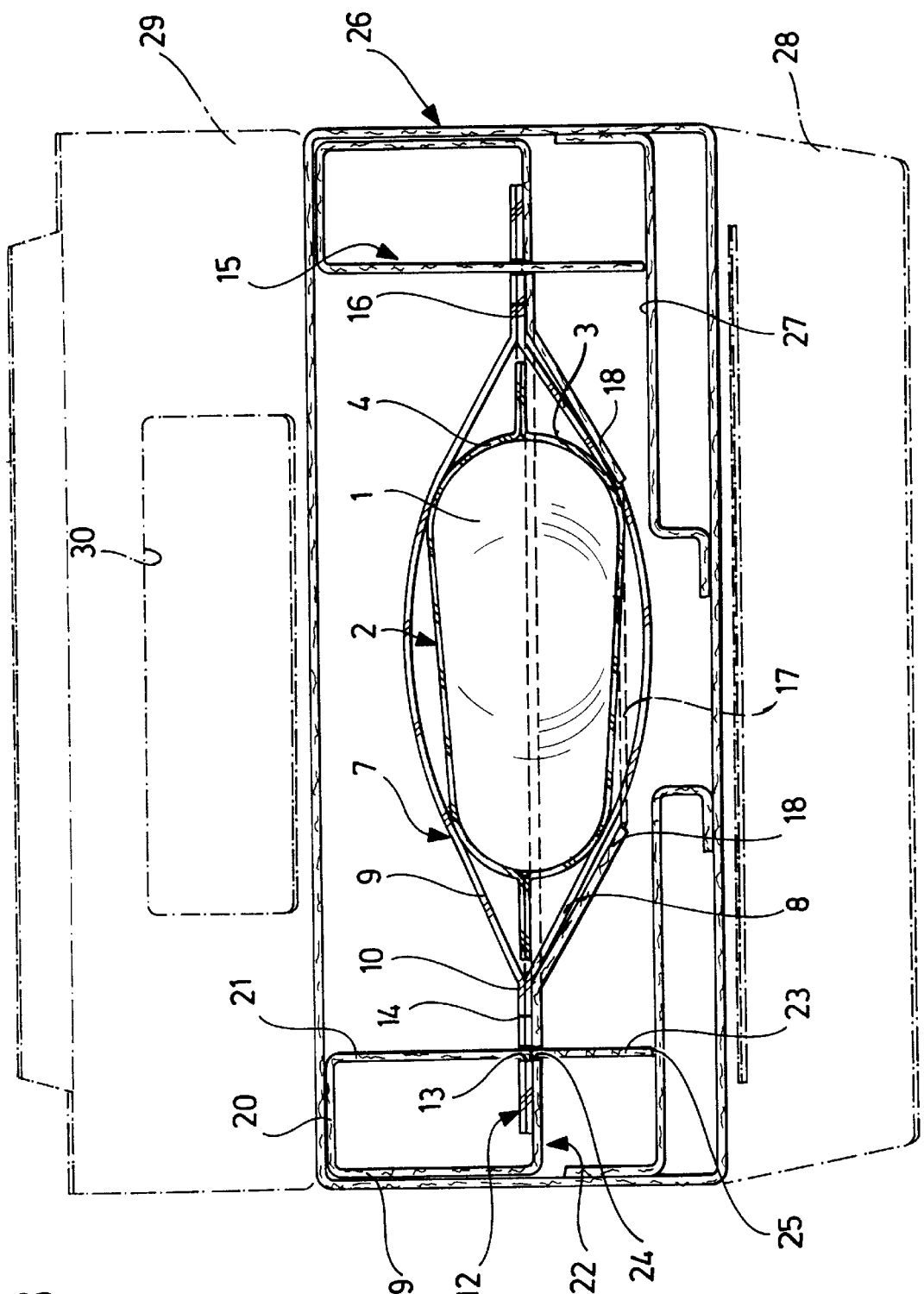
FIG. 3: a sectional view taken along line 3—3 in FIG. 2.

The packaging unit according to the invention will be described with reference to the packaging of a prosthetic shaft of a hip joint prosthesis, by way of example, as illustrated in the appended Figures. It will, however, be understood that any other article 1 to be packaged can be packed in a sterile condition with this packaging.

This article 1 is first placed in an inner bag 2 formed by two rectangular films 3, 4. These are joined surface-to-surface to one another in their edge areas, for example, by welding, so as to accommodate the article 1 between them. The interior of the inner bag 2 formed by the two films 3 and 4 is evacuated by suitable measures during the closing of the interior and then closed in a gastight manner. The article 1 is thereby fixed in its position in the inner bag 2.

In the area of the article 1, the two films 3 and 4 lie against it. In an adjacent area, on the other hand, they lie surface-to-surface against one another over the entire width of the inner bag 2. This area forms an extension 5 of the inner bag 2 into which a label 6 with a product description is inserted between the films 3 and 4. The label could also be attached to the outside of the films.

This inner bag 2 is placed in an outer bag 7 which is similarly formed by two films 8, 9 placed one on the other. These two films 8, 9 which likewise have a rectangular outer contour are joined surface-to-surface to one another, for example, by welding, along an edge strip 10 which runs parallel to the longitudinal edges of the films 8, 9 and surrounds the inserted inner bag 2, thereby lying tight against its outer contour so the inner bag 2 is fixed immovably in the interior of the outer bag 7. The outer bag 7 also has an extension 11 which receives the extension 5 of the inner bag 2.

At each of the two longitudinal edges of the outer bag 7, a longitudinal strip 12 projects over the edge strip 10 joining the two films. This longitudinal strip 12 is also formed by the two films 8, 9 lying surface-to-surface against one another. Immediately adjacent the edge strip 10 establishing the connection, a row of slot-shaped openings 13 is formed in the longitudinal strips 12. The longitudinal strips 12 are separated by a perforation line 14 from the rest of the outer bag 7. The perforation line 14 runs either through the openings 13 or past the openings 13 at the side facing the edge strip 10 of the outer bag 7.

The thus formed outer bag 7 forms together with the inner bag 2 accommodated in it a unit which can be handled independently and in which the article 1 packed twice in a sterile condition can be handled in the usual way.

For storage purposes, this packaging unit which can be handled independently is placed in a frame 15 which in the illustrated embodiment is in the form of a punched, folded part made, for example, of cardboard. This frame has a flat holding surface 16 with a central, rectangular opening 17, at whose edges flaps 18 integrally connected to the holding surface 16 pivot outwards at an incline from the plane of the holding surface 16. These flaps 18 thus form in the area of the central opening 17 a recess which is open downwards in the central area of the opening 17.

The side areas of the holding surface 16 are in the form of three parallel strips 19, 20, 21 folded through 900 in relation to one another so as to produce a closed reinforcement profile 22 of rectangular cross section at both longitudinal sides of the holding surface 16. Several lugs 23 are formed on the front strip 21, at the free edge thereof, and project over this free edge. The lugs 23 can be introduced into slot-shaped openings 24 in the holding surface 16 and pushed through these until they protrude with their free ends 25 like a foot downwards over the holding surface 16. They thus carry the frame 15 in such a way that the holding surface 16 and also the downwardly pivoted flaps 18 are arranged above a supporting surface on which the free ends are positioned.

The packaging unit consisting of outer bag and inner bag is fixed in such a way in this frame that the longitudinal strips 12 of the outer bag 7 lie surface-to-surface against the holding surface 16 of the frame 15, while the article 1 packed by the two bags is located in the area of the central opening 17. The openings 24 in the area of the surface 16 of the frame 15 are in alignment with the openings 13 in the longitudinal strip 12 of the outer bag 7 so it is possible to put the lugs 23 through these openings 13 in the longitudinal strip 12 and also through the openings 24 in the holding surface 16. The outer bag 7 is thereby immovably clamped in the frame 15. The article received by the outer bag is partly supported by the downwardly pivoted flaps 18, but is always held above a supporting surface on which the lugs 23 rest with their free ends 25.

The length of the central opening 17 is chosen to be of such size that it corresponds approximately to the length of the article 1 or is slightly larger than it.

The frame 15 is of such dimensions in its longitudinal direction that it receives the area of the two bags surrounding the article 1, while the extensions 5 and 11 protrude over the frame 15.

With the outer bag 7 clamped in the described way, the frame 15 can be pushed into a block-shaped, box-type storage container 26 which is likewise in the form of, for example, a folded cardboard box. This box has at its bottom end strip-shaped supporting surfaces 27 which extend parallel to the bottom and on which the free ends 25 of the lugs 23 stand, more specifically, in such a way that the frame 15 is fixed between these supporting surfaces 27 and the top side of the storage container 26. The width of the frame corresponds to the width of the storage container 26 so it is also fixed in the transverse direction. Finally, the frame 15 and the storage container 26 are of essentially identical length so as to also ensure fixing of the frame in the storage container 26 in the direction of insertion.

On its insertion side, the storage container 26 has at the top side and at the underside one flap 28, 29, respectively, adapted for swivel movement in front of the insertion side. In the swivelled-in state, the flaps 28, 29 lie in surface-to-surface contact against one another. The one flap 29 has a central opening 30 through which the flap 28 is visible when the flaps are closed.

To close the flaps 28 and 29, the procedure is as follows: The first closed flap 28 positions the extensions 5, 11 of the bags hanging out of the insertion opening of the storage container 26 against the top side of the storage container 26 so that during closure of the flap 29 with the opening 30, the extensions 5, 11 are turned over onto the inside flap 28 so these extensions lie surface-to-surface between the two flaps 28 and 29. The label 6 enclosed in the extensions is then located directly behind the opening 30 so this label is visible through the opening 30 when the storage container 26 is closed.

The article packed in a sterile condition can be stored in a safe way in this storage container, in particular, mechanical damage to the article packed in a sterile condition is excluded.

To remove the article, the frame 15 is pulled out of the storage container 26, and the outer bag 7 is then separated along the perforation lines 14 from the longitudinal strips 12 so that the still closed outer bag can be taken out of the frame 15 without the lugs 23 having to be pulled out of the openings 13 and the openings 24.

At this stage, the article is still packed in a sterile state, but it is now convenient for handling and so the article can be transported to the place of use and finally removed from the films there and used as required.

In principle, the frame and the storage container are reusable. The only waste occurring are the films, which are of slight volume and, given a suitable choice of material, can be recycled.

What is claimed is:

1. A packaging unit for an article to packed in a sterile condition, comprising:
    an inner bag adapted to receive and surround the article to be packed;
    said inner bag adapted to be evacuated and sealed in a gastight manner to tightly enclose the article;
    a closed outer bag adapted to receive said inner bag;
    a shape-retaining frame for holding said outer bag essentially immovably; and
    a shape-retaining storage container; wherein:
    said frame is insertable into said shape-retaining storage container.

2. The packaging unit of claim 1, wherein:
    said frame is in the form of a slide which is slidable into said storage container.

3. The packaging unit of claim 1, wherein:
    said inner bag and said outer bag are so adapted to one another in their shape that said inner bag is immovably held in place in said outer bag.

4. The packaging unit of claim 1, wherein:
    said inner bag comprises two film layers which are placed one on top of the other, and are joined to one another along respective edges thereof.

5. The packaging unit of claim 4, wherein:
    said film layers are joined to one another so as to lie surface-to-surface against one another along an edge strip surrounding an interior of the inner bag.

6. The packaging unit of claim 1, wherein:
    said outer bag comprises two film layers lying one on top of the other, and joined to one another along respective edges thereof.

7. The packaging unit of claim 6, wherein:
    said film layers are joined to one another so as to lie surface-to-surface against one another along an edge strip surrounding an interior of the inner bag.

8. The packaging unit of claim 1, wherein:
    said outer bag has, in an edge area thereof, openings through which projections pass in order to fix said outer bag on said frame.

9. The packaging unit of claim 8, wherein:
    said edge area having said openings is separated from the rest of said outer bag by perforation lines.

10. The packaging unit of claim 8, wherein:
    said openings are arranged at opposite side strips of said outer bag.

11. The packaging unit of claim 1, wherein:
    said inner bag is rectangular.

12. The packaging unit of claim 1, wherein:
    said outer bag is rectangular.

13. The packaging unit of claim 1, wherein:
    at least one of said inner bag and said outer bag carry, at one side thereof, a lug-shaped extension for receiving a label.

14. The packaging unit of claim 13, wherein:
    said inner bag and said outer bag each carry respective lug-shaped extensions for receiving a label; and
    the lug-shaped extension of said inner bag is enclosed in the lug-shaped extension of said outer bag.

15. The packaging unit of claim 13, wherein:
    the lug-shaped extension of said at least one of said inner bag and said outer bag protrudes beyond an edge of said frame.

16. The packaging unit of claim 1, wherein:

at least one of said inner bag and said outer bag comprises a material which is adapted to be sterilized by radiation.

17. The packaging unit of claim 1, wherein:

said frame has a central opening, and a holding surface which surrounds said central opening, and an edge area of said outer bag is fixable on said holding surface such that said inner bag is arranged in an area of said central opening.

18. The packaging unit of claim 17, wherein:

said central opening is delimited, at least in part, by flaps which are connected to said holding surface.

19. The packaging unit of claim 18, wherein:

said flaps are pivoted at an incline to said holding surface.

20. The packaging unit of claim 17, further comprising:

reinforcement profiles adjoining two opposite longitudinal sides of said frame.

21. The packaging unit of claim 20, wherein:

said reinforcement profiles are formed by parallel, folded-over strips in an edge area of said holding surface.

22. The packaging unit of claim 8, wherein:

said projections for fixing said outer bag on said frame pass through openings in said frame which are in alignment with said openings on said outer bag.

23. The packaging unit of claim 21, wherein:

said outer bag has, in an edge area there of, openings through which projections pass in order to fix said outer bag on said frame; and said projections are formed by lugs at a free edge of said parallel, folded over strips of said reinforcement profiles.

24. The packaging unit of claim 23, wherein:

said lugs are of such length that, in the state in which they pass through said openings of said outer bag and said openings of said frame, said lugs protrude downwardly beyond said holding surface of said frame and form standing legs for said frame.

25. The packaging unit of claim 24, wherein:

said lugs protrude downwardly beyond the contour of said outer bag which is held in said frame and receives said inner bag with said article therein.

26. The packaging unit of claim 1, wherein:

said storage container is block-shaped.

27. The packaging unit of claim 1, wherein:

said storage container has supporting surfaces extending parallel to its bottom for receiving said frame.

28. The packaging unit of claim 1, wherein:

said storage container is closable at its end faces by two flaps which, in a closed state, lie surface-to-surface against one another.

29. The packaging unit of claim 28, wherein:

one of the flaps is an outer flap having an opening through which a flat data carrier inserted between said flaps is visible.

30. The packaging unit of claim 29, wherein:

said data carrier is formed by an extension of at least one of said inner bag and said outer bag with a label inserted therein.

31. The packaging unit of claim 1, wherein:

said frame is selected from the group consisting of cardboard and plastic.

32. The packaging unit of claim 1, wherein:

said storage container is selected from the group consisting of cardboard and plastic.

* * * * *